US012035991B2

(12) United States Patent
Ergueta Tejerina et al.

(10) Patent No.: US 12,035,991 B2
(45) Date of Patent: Jul. 16, 2024

(54) DETECTING CABLE BREAKAGE ON CABLE DRIVEN TOOLS

(71) Applicant: Verb Surgical Inc., Santa Clara, CA (US)

(72) Inventors: Edgar Ignacio Ergueta Tejerina, San Jose, CA (US); Alireza Hariri, Berkeley, CA (US)

(73) Assignee: Verb Surgical Inc., Santa Clara, CA (US)

( * ) Notice: Subject to any disclaimer, the term of this patent is extended or adjusted under 35 U.S.C. 154(b) by 717 days.

(21) Appl. No.: 16/818,938

(22) Filed: Mar. 13, 2020

(65) Prior Publication Data

US 2021/0282876 A1 Sep. 16, 2021

(51) Int. Cl.
```
A61B 34/00      (2016.01)
A61B 17/28      (2006.01)
A61B 17/3201    (2006.01)
A61B 34/30      (2016.01)
A61B 17/00      (2006.01)
A61B 34/37      (2016.01)
```
(52) U.S. Cl.
CPC ............ *A61B 34/71* (2016.02); *A61B 17/28* (2013.01); *A61B 17/3201* (2013.01); *A61B 34/30* (2016.02); *A61B 2017/00725* (2013.01); *A61B 34/37* (2016.02); *A61B 2034/715* (2016.02)

(58) Field of Classification Search
CPC ......... A61B 34/30; A61B 34/37; A61B 34/71; A61B 2034/715; A61B 17/28; A61B 17/3201; A61B 2017/00725; A61B 2090/064; B25J 9/104; B25J 9/1633

USPC ........................................................ 606/174
See application file for complete search history.

(56) References Cited

U.S. PATENT DOCUMENTS

| | | | |
|---|---|---|---|
| 2012/0071895 A1* | 3/2012 | Stahler | A61B 34/20 606/130 |
| 2014/0357953 A1* | 12/2014 | Roelle | A61B 1/0051 600/118 |
| 2016/0287840 A1 | 10/2016 | Jiang | |
| 2017/0100197 A1* | 4/2017 | Zubiate | A61B 34/37 |
| 2019/0274769 A1 | 9/2019 | Perdue et al. | |
| 2021/0052340 A1* | 2/2021 | Rabindran | A61B 34/71 |

FOREIGN PATENT DOCUMENTS

WO        2018148030        8/2018

OTHER PUBLICATIONS

International Search Report and Written Opinion for International Application No. PCT/US2020/023595 mailed Dec. 4, 2020, 16 pages.
International Preliminary Report on Patentability for International Application No. PCT/US2020/023595 mailed Sep. 22, 2022, 9 pages.

* cited by examiner

*Primary Examiner* — Kankindi Rwego
(74) *Attorney, Agent, or Firm* — Aikin & Gallant, LLP

(57) ABSTRACT

A surgical robotic tool used with a surgical robotic system can include cables that effect movement in the surgical robotic tool. A brake in any of these cables can be detected by checking a plurality of conditions. A process can compare a) a tension error against a first threshold, b) a rate of change of the sensed tension of the cable against a second threshold, and c) a rate of change of a cable extension error against a third threshold. If all thresholds are exceeded, the process can disable the respective actuator.

20 Claims, 8 Drawing Sheets

DETECTING CABLE BREAKAGE ON CABLE DRIVEN TOOLS

TECHNICAL FIELD

This disclosure relates generally to the field of surgical robotics and, more particularly, to detection of cable breakage on cable driven tools for use with a surgical robotic system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with surgical robotic systems that include one or more robotic arms for manipulating surgical instruments based on commands from an operator.

In a surgical robotic system, a surgical tool can attach to a surgical robotic arm. Such a tool can be used to enter, view, or manipulate an internal anatomy of the patient. The surgical tool can be driven with cables to effect movement.

SUMMARY

Generally, failure in cables used to move surgical robotic tools can be detected by checking a plurality of conditions. A system or method can check a tension, a rate of change of tension, and a rate of change of a cable extension error for any cable to be monitored. When all conditions indicate a failure (e.g., exceed respective thresholds), then the system can take remedial measures. For example, an actuator that is coupled to the cable can be disabled, thereby reducing the risk of further movement when the cable has been compromised. Other aspects are described.

BRIEF DESCRIPTION OF THE DRAWINGS

FIGS. 7A-7D show cable extension error when a cable fails.

DETAILED DESCRIPTION

Non-limiting examples of various aspects and variations of the invention are described herein and illustrated in the accompanying drawings.

Figure 1:
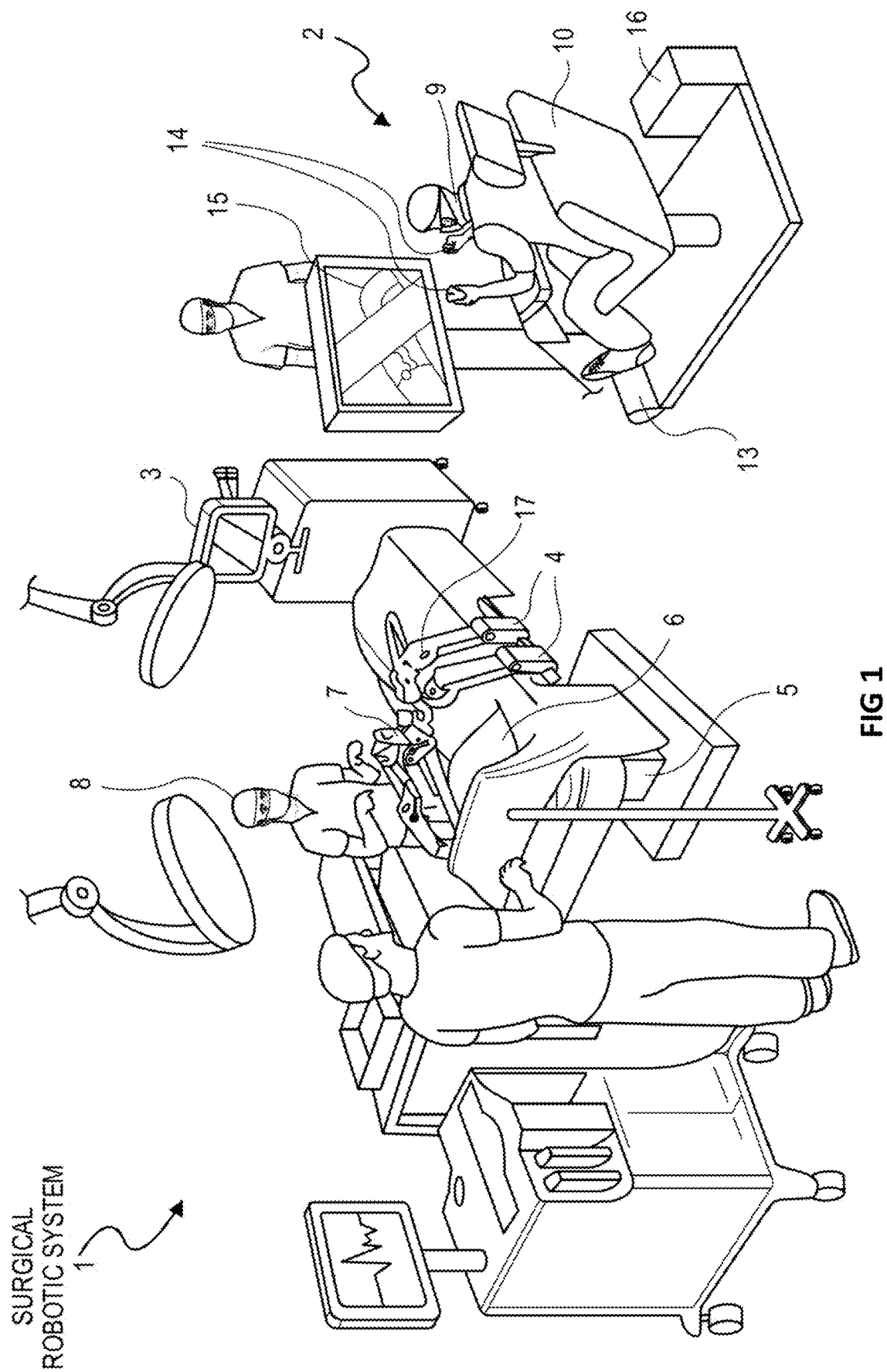
FIG. 1 is a pictorial view of an example surgical robotic system in an operating arena.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In one embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 or the attached surgical tools 7, e.g., teleoperation. The user console 2 may be located in the same operating room as the rest of the system 1, as shown in FIG. 1. In other environments, however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired or wireless links, using any suitable ones of a variety of data communication protocols. Any wired connections may be optionally built into the floor or walls or ceiling of the operating room. The robotic system 1 may provide video output to one or more displays, including displays within the operating room as well as remote displays that are accessible via the Internet or other networks (e.g., the robotic system 1 can include one or more endoscopic cameras that provide video output or other suitable image data to the displays). The video output or feed may also be encrypted to ensure privacy and all or portions of the video output may be saved to a server or electronic healthcare record system.

Figure 2:
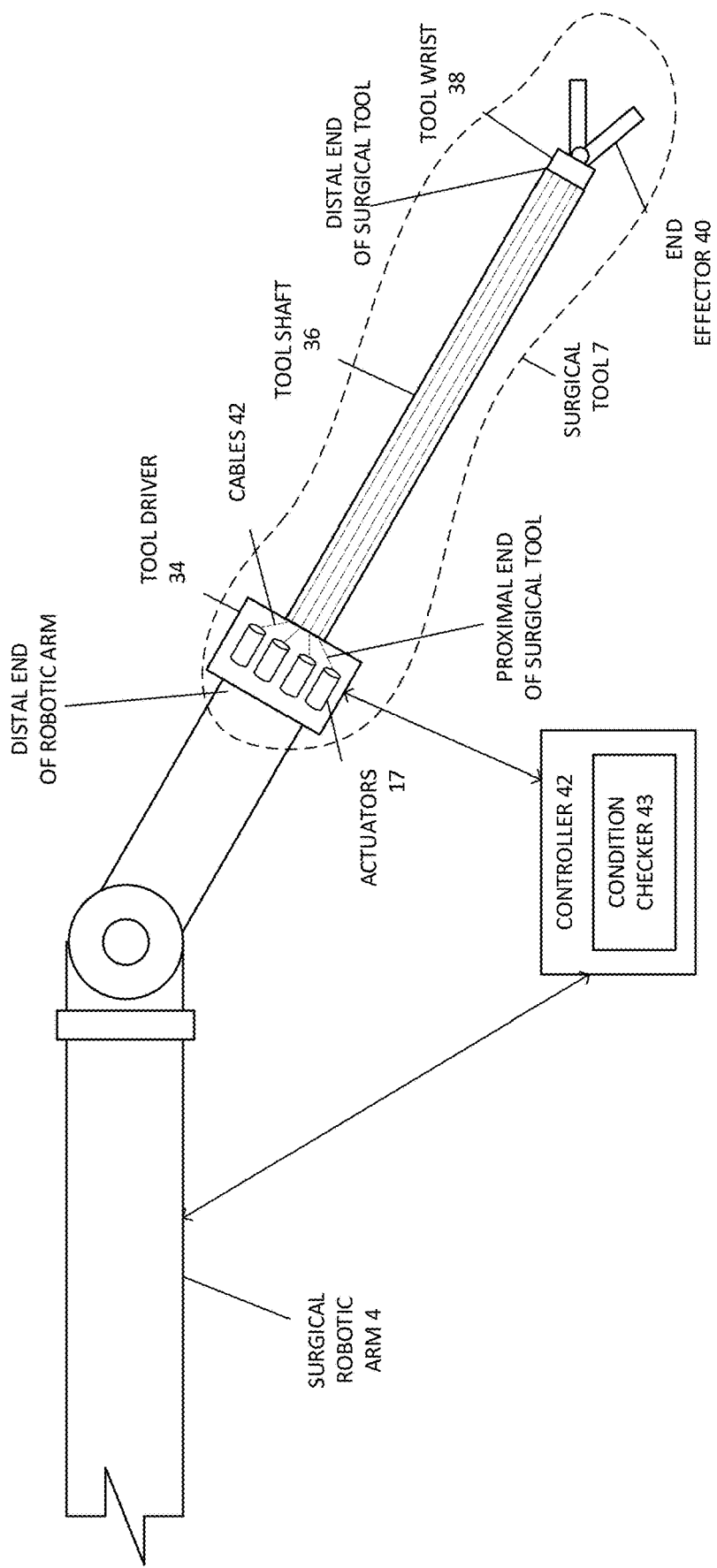
FIG. 2 shows an example of a surgical robotic arm and tool according to some embodiments.

Referring to FIG. 2, a surgical robotic arm with an attached surgical tool is shown according to some embodiments. Surgical robotic arm 4 can connect at a distal end to surgical tool 7. Actuators 17 can include actuators of the surgical robotic arm that effect movement in joints of the surgical robotic arm. Actuators 17 also includes surgical tool actuators, which are shown in FIG. 2.

The actuators of the surgical tool can be housed in a tool driver 34. The actuators are controlled by controller 42. In some embodiments, the controller 42 can be integrated as part of the surgical robotic system control tower or console compute system. In other embodiments, this controller can be a standalone controller, having one or more processors. The controller can generate commands that are received by the actuators to effect movement in the actuators. Each command can specify an amount and direction of movement to coordinate desired movement in the surgical robotic tool.

The surgical tool can include a plurality of cables 42. The cables can be housed in a tool shaft 36, which can be an elongated member having one or more channels to house the cables. Each cable is coupled to i) a respective tool actuator at a proximal end of the tool, and ii) an end effector 40 of the tool at a distal end of the tool, such that the respective actuator effects a movement of the end effector through the cables.

For example, the actuators can transfer forces in the cables in a coordinated manner to generate a pitch or a yaw movement at the tool wrist 38, providing angle manipulation of the tool during surgery. The actuators can also cause jaw movement (e.g., opening and closing) of the end effector, which can include a grasper or a cutter. Thus, the cable actuated tool can grasp or cut within a surgical site at a variety of angles. The number of cables can vary based on application. In some embodiments, there are four or more cables. In some embodiments, three cables can be dedicated to tool wrist movement. In some embodiments, one cable can be dedicated to jaw movement such that, when used in combination with a spring, can create opening and closing jaw movement.

The controller can have a condition checker 43 that receives and processes cable information from the tool to detect cable breakage. The cable information be compared to different conditions, and if the conditions are all met, then the condition checker can determine that a cable has failed. The controller can sense the moment right before and/or when the cable breaks and take immediate remedial measures to reduce risk of injury to a patient.

Figure 3:
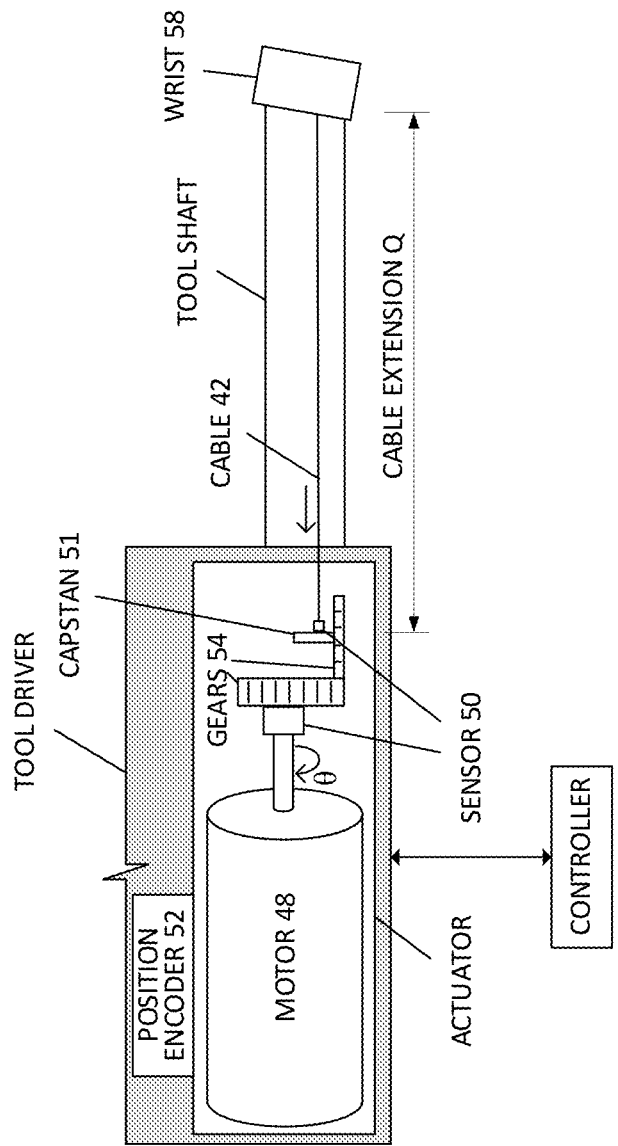
FIG. 3 shows an example of a tool according to some embodiments.

FIG. 3 shows an actuator in one embodiment. The illustration shows general representations of an actuator and components. This actuator can represent one or more of the actuators shown in FIG. 1 and FIG. 2. Still referring to FIG. 3, the actuator can include a motor 48 that rotates an angle $\theta$ in a direction and/or an amount that is specified in a controller command.

Tension of each cable can be sensed by any of sensors 50, which can include a tension sensor that is coupled to a respective cable or a torque sensor that measures torque of a respective motor coupled to the cable. Measured torque (a rotational force) can be converted to tension (a linear force). Each cable can have an initial tension (a pre-tension) at a starting 'relaxed' position of the tool. In some embodiments, the pre-tension Tp is 10N. A tension error can be determined as a difference between the pre-tension and a current sensed tension, which can be expressed as $\Delta T = Tp - Ts$. This tension error can represent a tension drop in the cable.

In some embodiments, where the tool does not require cable pre-tension, the pre-tension can be zero. Thus, in this case, delta tension can be the sensed tension.

The controller can determine a measured cable extension q based on measured cable position x, the sensed cable tension T, and a known cable stiffness constant Ke. In some embodiments, measured cable extension q can be determined through the following equation: $q = x - T/Ke$.

Measured cable position x can be determined based in on actuator position $P_A$ and a capstan radius $r_c$. The capstan radius is a radius of capstan 51, upon which a respective cable fixes to and wraps around when the capstan rotates. Rotation of the capstan can be effected through one or more gears 54 that translate rotational motion of motor 48 to rotational motion of the capstan. When the capstan is rotated, cable position and cable tension changes accordingly, depending on an amount and direction of rotation. In some embodiments, measured cable position x is determined through the equation: $x = P_A * r_c$.

Actuator position $P_A$ can be determined based on a position P encoded from a position encoder 52, a known gear ratio (Gr) of the actuator, and an offset (e.g., determined through calibration). The position encoder can be a rotary position encoder that monitors motor shaft position and encodes the current motor shaft position, e.g., to a value representing angular position. In some embodiments, actuator position $P_A$ can be determined through the following equation: $P_A = P/Gr + \text{offset}$.

The controller can generate a joint command (Jcmd) such as 'close jaw by X degrees', 'roll wrist by X degrees', etc. The joint command is a command in 'joint space' that can be translated to physical space using a kinematics model (an inverse kinematics matrix B'). A modeled cable extension $q_{cmd}$ can be determined through the following equation: $q_{cmd} = (B'^* Jcmd) * r_c$. This modeled cable extension represents a desired cable extension. It should be understood that a cable extension describes how much a cable is stretching, while a measured cable position describes how much displacement has been placed on the cable by the actuator.

Robot kinematics relates the dimensions and connectivity of kinematic chains to the position, velocity and acceleration of each link in a robotic system. This allows planned and controlled movement of the robot. Kinematics equations can be non-linear equations that map the joint parameters to the configuration of the robot system. Forward kinematics uses the kinematic equations of a robot to compute the position of the end-effector from specified values for the joint parameters. The reverse process that computes the joint parameters that achieve a specified position of the end-effector is known as inverse kinematics. The dimensions of the robot and its kinematics equations define the volume of space reachable by the robot, known as its workspace.

A cable extension error $\Delta q$ can be determined, representing a difference between measured cable extension q and modeled cable extension $q_{cmd}$. In some embodiments, $\Delta q$ can be expressed as $\Delta q = \text{abs}(q - q_{cmd})$.

The tension error $\Delta T$, cable extension error $\Delta q$, and derivatives thereof can be monitored by the controller to determine whether or not a cable break has occurred. These conditions can be monitored over a period of time which can be formed through consecutive samples. If, over a predefined number of samples, these conditions (tension error $\Delta T$, cable extension error $\Delta q$, and derivatives thereof) exceed respective thresholds, then the controller can flag a cable failure fault and disable a respective actuator. This process is further described in FIG. 4 and FIG. 5.

Figure 4:
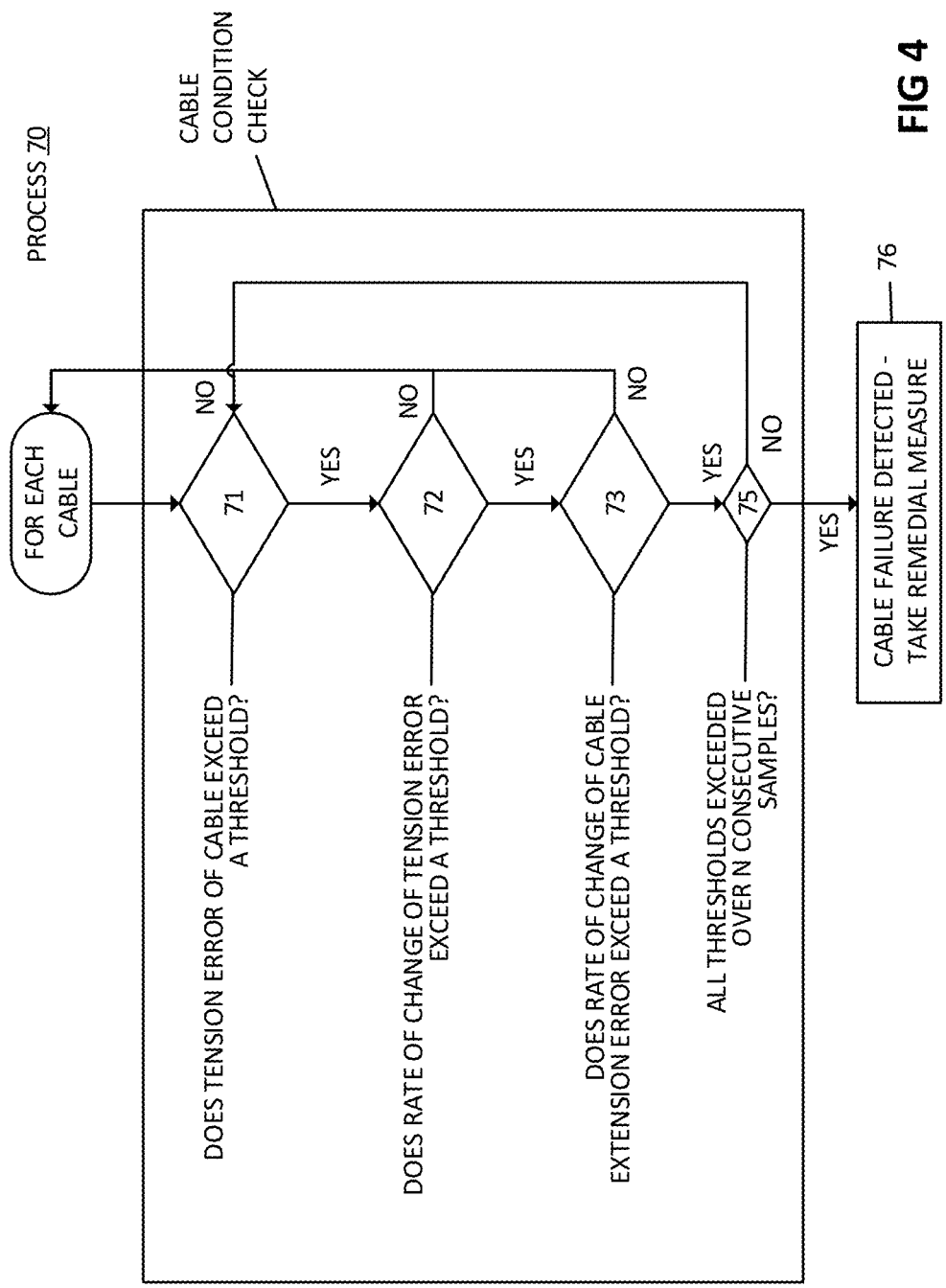
FIG. 4 shows a process for detection of cable failure according to some embodiments.

In FIG. 4, a process is shown that detects cable brake in a cable-driven surgical robotic tool by performing a series of operations. For each cable, a cable condition check can be performed. The order in which operations 71, 72, and 73 are performed relative to each other can vary. For example, operation 71 need not be performed first, and operation 73 need not be performed last.

Operation 71 includes comparing a tension error $\Delta T$ against a first threshold, wherein the tension error is a difference between a pre-tension and a sensed tension of the cable. The sensed tension can be sensed through a torque or tension sensor, as discussed. The pretention is an initial tension of the cable when resting e.g., at a default position of the tool.

Operation 72 includes comparing a rate of change of the sensed tension of the cable against a second threshold. This rate of change can be a time derivative of the sensed cable tension, and can be expressed as $dTs/dt$, where Ts is the sensed tension of a respective cable, as described earlier. The second threshold can be expressed as $dT/dt$, where T is a measure of force, typically in Newtons. When the rate of change of the sensed tension exceeds the second threshold, this can indicate a failure in the respective cable, if the other conditions for failure detection also indicate the same.

Operation 73 includes comparing a rate of change of a cable extension error $\Delta q$ against a third threshold. The cable extension error $\Delta q$ can be a difference between a modeled cable extension $q_{cmd}$ and a measured cable extension q. In some embodiments, the cable extension error is determined based on an absolute value of the difference. This error can be expressed in terms of length (e.g., mm).

As discussed in other sections, the measured cable extension q can be determined based on a measured cable position (derived from actuator position), the sensed tension of the cable, and a cable stiffness. The actuator position can be determined by a position encoder of the actuator. The cable stiffness can be a known constant, and the tension can be sensed with a sensor.

The modeled cable extension is determined based on a joint command and a kinematics translation that converts the joint command to a physical measurable parameter (e.g., rotation or distance). In some embodiments, the joint command is an angular position of a motor. As described, the physical parameter can be applied to a capstan radius to yield the modeled cable extension.

The rate of change of the cable extension error can be a time derivative of $\Delta q$, which can be expressed as $d\Delta q/dt$. Thus, the third threshold can be expressed as a time derivative of length, or $ds/dt$ where s is a length (e.g., in mm). This indicates how fast the cable is sensed to be stretching relative to how fast the cable should be stretching given a command and known kinematics of the surgical tool.

Block 75 shows that the condition check (of all conditions and respective thresholds) can be performed repeatedly over a time window, which can also be defined as a number of consecutive samples N. For example, this check of all thresholds can be performed over 30, 35, or 40 consecutive samples. The number of consecutive samples can vary depending on application, for example, based on tool, or how often each sample is taken. If all thresholds are exceeded for N number of consecutive samples, then the system can proceed to operation 76.

Operation 76 includes flagging that a cable failure is detected at a respective cable at which all thresholds were exceeded over consecutive samples. Remedial measures are taken, including disabling at least the respective actuator. This can be performed immediately, so as to reduce risk of unwanted movement during surgery, and reduce additional damage to the surgical tool. By requiring failure of all of these conditions in consecutive frames, the process reduces false positives that can be caused by normal use of the surgical tool. It should be understood that for each cable, this process is performed over consecutive samples. Thus, one cable can be flagged as failing over N samples, while over the same time period, another cable does not fail. The respective actuator connected to the failed cable can be disabled. In some embodiments, other actuators (in addition to the actuator that is connected to the failed cable) can be disabled, to prevent less predictable movement of the tool that could be result at the end effector due to the broken cable.

Figure 5:
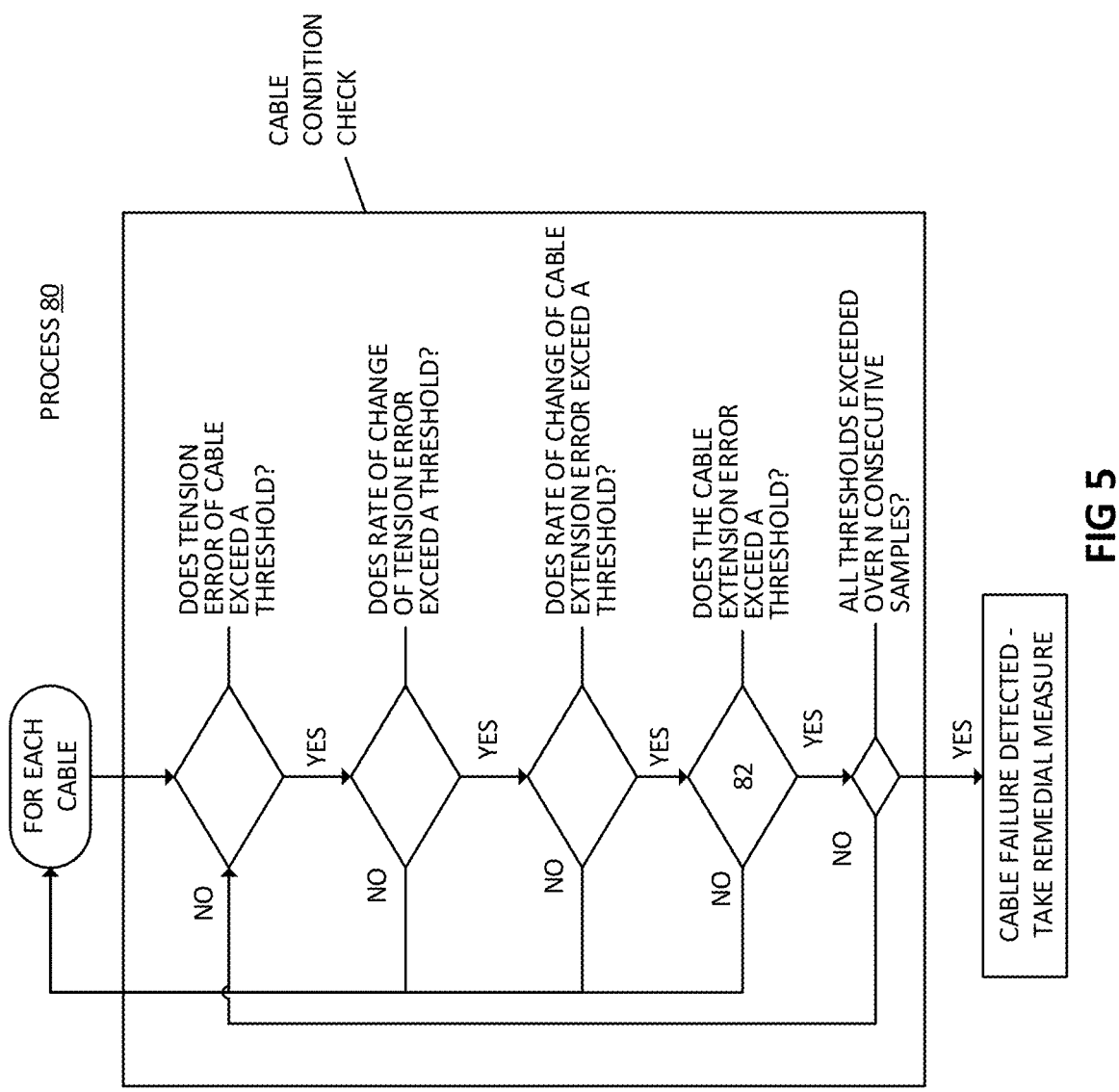
FIG. 5 shows a process for detection of cable failure according to some embodiments.
Figure 6A:
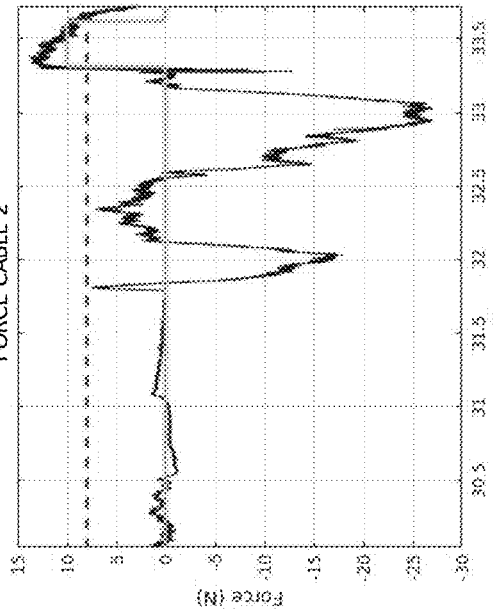
FIGS. 6A-6D show force of cables when a cable fails.
Figure 6C:
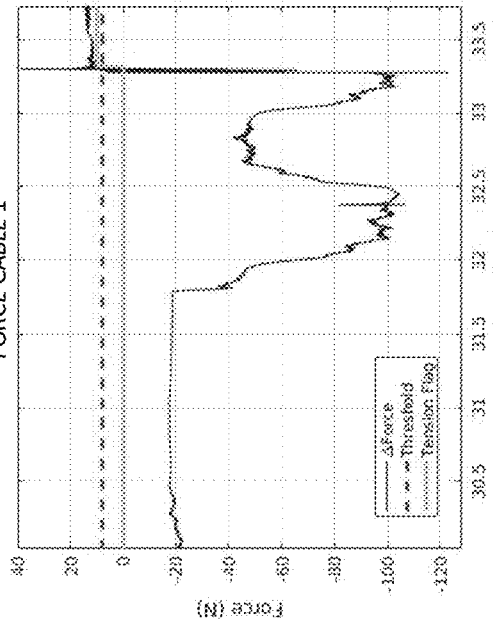
Figure 6B:
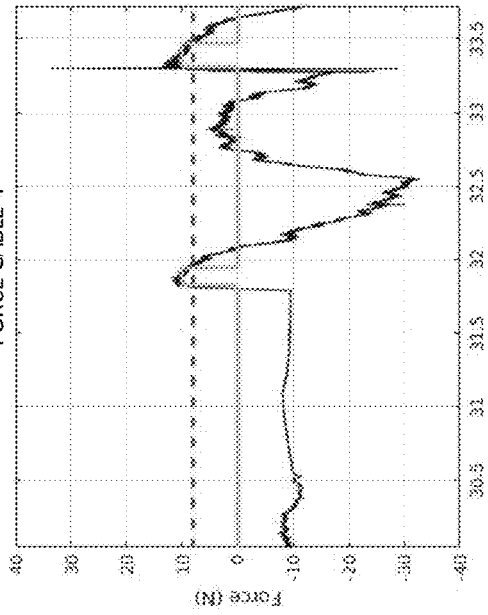
Figure 6D:
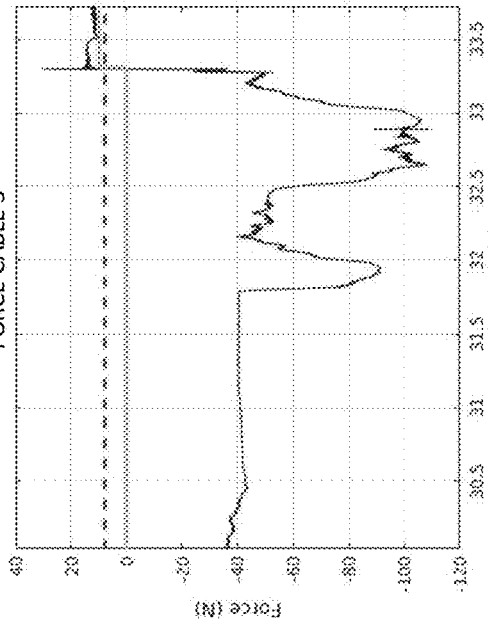

FIG. 5 shows a process 80 for detecting cable breakage, similar to that shown in FIG. 4. This process includes an additional condition checked at operation 82. At operation 82, the process includes comparing the cable extension error against a fourth threshold, which can be determined as difference between modeled cable extension and measured cable extension. Thus, this process accounts for the difference between modeled cable extension and measured cable extension, in addition to the rate of change thereof, which can further reduce false positives. When all conditions are shown to fail, then the system can take remedial measures, as described with respect to FIG. 4.

FIGS. 6A-6D show force of cables when cables break. The red dotted line shows a threshold, and the y-axis represents the tension error of the cable. These examples show why requiring both the tension error and time derivative thereof can avoid false positives. In some cases, the threshold can be exceeded without break. In other cases, the rate of change might be high without cable breakage.

Figure 7A:
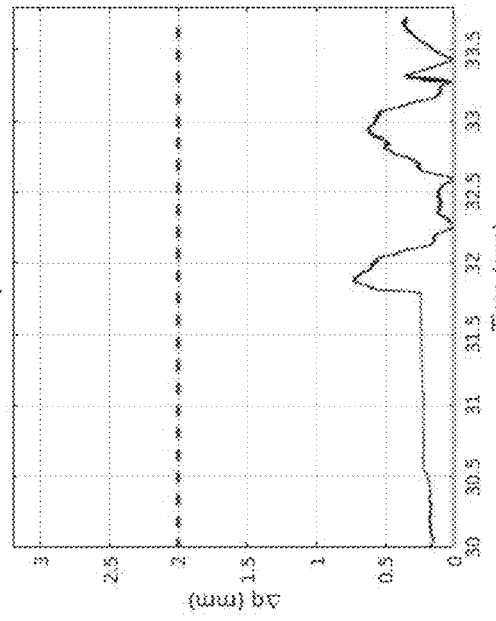
Figure 7B:
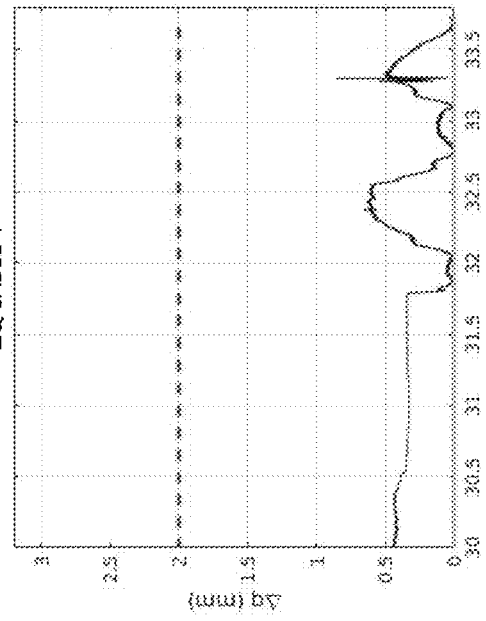
Figure 6C:
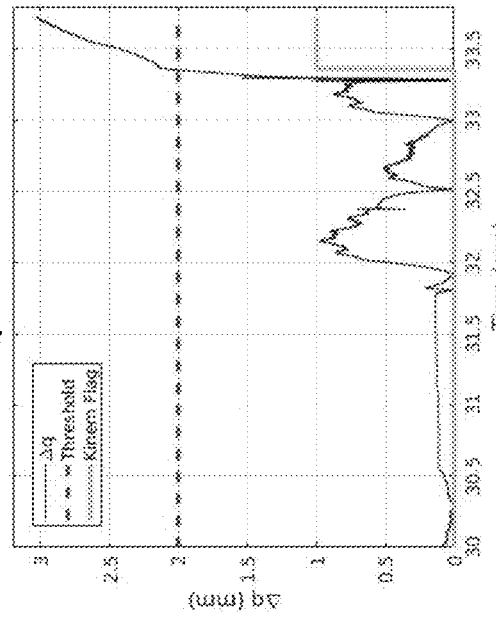
Figure 7D:
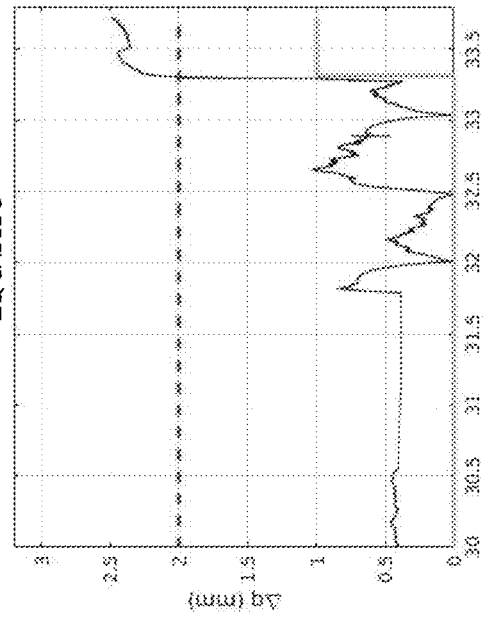
Figure 8B:
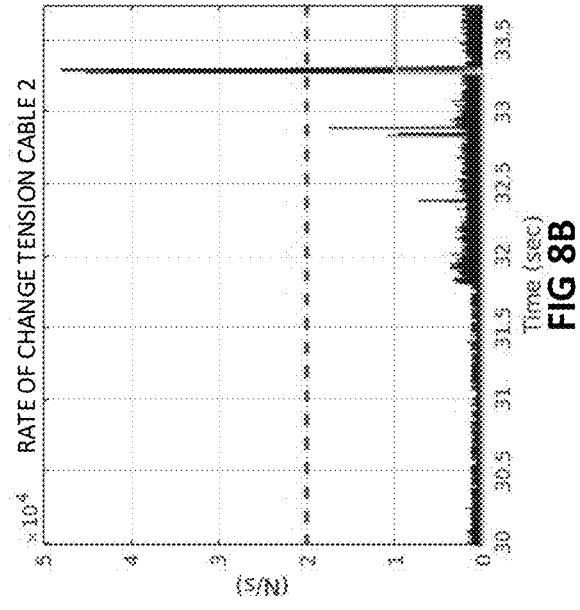
FIGS. 8A-8D shows a rate of change of cable tension when a cable fails.
Figure 8D:
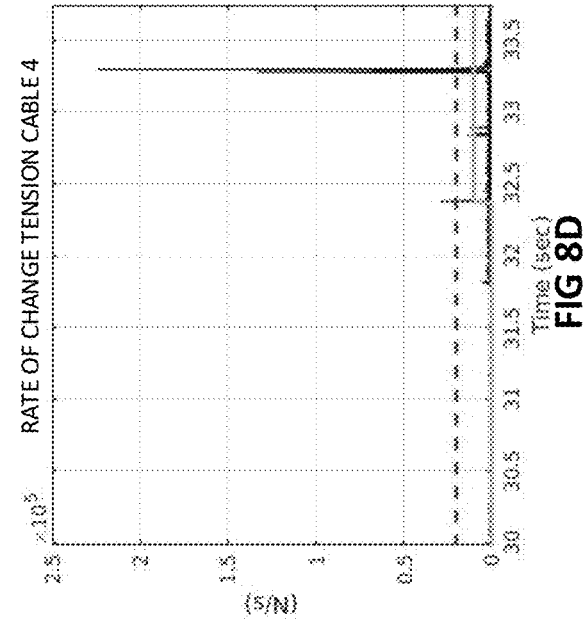
Figure 8A:
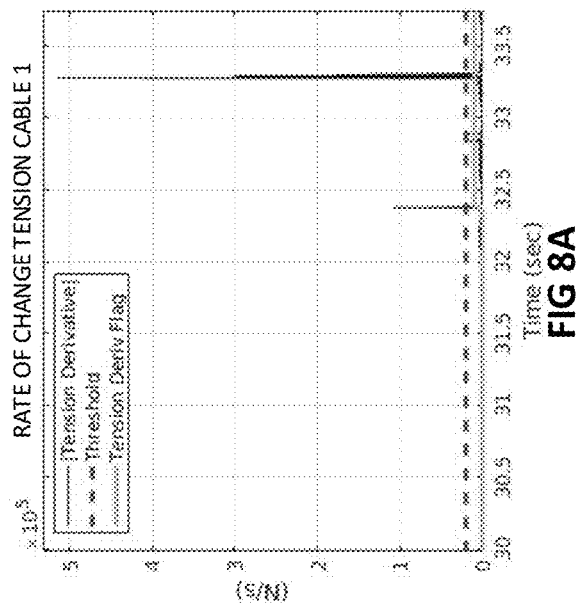
Figure 8C:
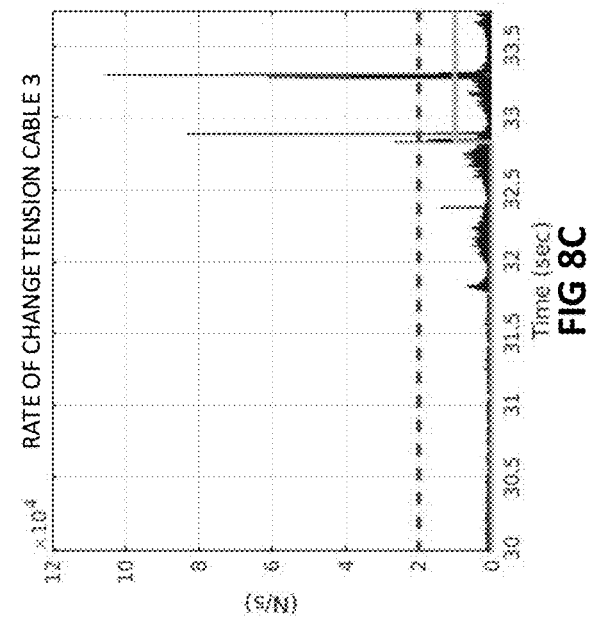

FIGS. 7A-7D shows cable extension error, which is difference between modeled and measured cable extension, when a cable fails. Note the sharp increase on cable extension error, which can be defined by the time derivative of the cable extension error, when a cable approaches a break (as shown in FIG. 7A and FIG. 7C).

FIGS. 8A-8D shows a rate of change of cable tension for different cables during failure. The cable tension here is the sensed tension of the cable. As shown, the rate of change of the cable tension with respect to time sharply increases right before the cable breaks.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A surgical robotic system comprising:
    a surgical robotic tool comprising a plurality of cables, each cable coupled to i) a respective actuator at a proximal end, and ii) an end effector of the tool at a distal end, such that the respective actuator effects a movement of the end effector; and
    one or more processors configured to:
    for each cable of the plurality of cables, determine:
        a cable extension error as a difference between a modeled cable extension of the cable that is modeled based on a kinematics translation and a measured cable extension of the cable,
        a tension error as a difference between a pre-tension and a sensed tension of the cable,
        a rate of change of the sensed tension of the cable, and
        a rate of change of the cable extension error,
    detect a break in a respective cable in response to 1) the corresponding tension error of the respective cable exceeding a first threshold, 2) the corresponding rate of change of the sensed tension of the respective cable exceeding a second threshold, and 3) the corresponding rate of change of the cable extension error exceeding a third threshold, wherein the corresponding tension error, the corresponding rate of change of the sensed tension, and the corresponding rate of change of the cable extension error are used to detect the break in the respective cable to avoid or reduce false positives, and
    in response to the detected break, disable the respective actuator associated with the respective cable.

2. The surgical robotic system of claim 1, wherein the measured cable extension is determined based on a sensed cable position, the sensed tension of the cable, and a cable stiffness.

3. The surgical robotic system of claim 2, wherein the kinematics translation maps a command to the respective actuator to the modeled cable extension.

4. The surgical robotic system of claim 1, wherein the one or more processors is further configured to disable the respective actuator only when all of 1) the corresponding tension error of the respective cable exceeds the first threshold, 2) the corresponding rate of change of the sensed tension of the respective cable exceeds the second threshold, 3) the corresponding rate of change of the cable extension error exceeds the third threshold, and 4) the corresponding cable extension error of the respective cable exceeds a fourth threshold.

5. The surgical robotic system of claim 1, wherein each of the plurality of cables are loaded with the pre-tension of 10N.

6. The surgical robotic system of claim 1, wherein the surgical robotic tool includes at least one of: a grasper, a hook, scissors, or a cutter.

7. The surgical robotic system of claim 6, wherein the movement of the end effector is a jaw movement of the grasper, the hook, the scissor, or the cutter of the surgical robotic tool.

8. The surgical robotic system of claim 1, wherein the movement of the end effector is a pitch or a yaw movement at a wrist of the surgical robotic tool.

9. The surgical robotic system of claim 1, wherein the plurality of cables includes four or more cables.

10. A method performed for detecting failure with a surgical robotic tool having a plurality of cables, each cable coupled to i) a respective actuator at a proximal end, and ii) an end effector of the surgical robotic tool at a distal end, such that the respective actuator effects a movement of the end effector, the method comprising:

for each cable of the plurality of cables, determining:
a cable extension error as a difference between a modeled cable extension of the cable that is modeled using a kinematics translation and a measured cable extension of the cable,
a tension error as a difference between a pre-tension and a sensed tension of the cable,
a rate of change of the sensed tension, and
a rate of change of the cable extension error;
detecting a break in a respective cable in response to 1) the corresponding tension error of the respective cable exceeding a first threshold, 2) the corresponding rate of change of the sensed tension of the respective cable exceeding a second threshold, and 3) the corresponding rate of change of the cable extension error exceeding a third threshold, wherein the corresponding tension error, the corresponding rate of change of the sensed tension, and the corresponding rate of change of the cable extension error are used to detect the break in the respective cable to avoid or reduce false positives, and
in response to the detected break, disabling the respective actuator associated with the respective cable.

11. The method of claim 10, wherein the measured cable extension is determined based on a sensed cable position, the sensed tension of the cable, and a cable stiffness.

12. The method of claim 11, wherein the modeled cable extension is determined based at least on an angular position of a motor of the respective actuator and the kinematics translation that converts the angular position to the modeled cable extension.

13. The method of claim 10 further comprising
disabling the respective actuator when all of 1) the corresponding tension error of the respective cable exceeds the first threshold, 2) the corresponding rate of change of the sensed tension of the respective cable exceeds the second threshold, 3) the corresponding rate of change of the cable extension error exceeds the third threshold, and 4) the corresponding cable extension error of the respective cable exceeds a fourth threshold.

14. The method of claim 10, wherein the pre-tension of each cable is 10N and the first threshold is 8N.

15. The method of claim 10, wherein the surgical robotic tool includes at least one of: a grasper, a hook, a scissor, or a cutter.

16. The method of claim 15, wherein the movement of the end effector is a jaw movement of the grasper, the hook, the scissor, or the cutter of the surgical robotic tool.

17. The method of claim 10, wherein the movement of the end effector is a pitch or a yaw movement at a wrist of the surgical robotic tool.

18. The method of claim 10, wherein the plurality of cables includes four or more cables.

19. The method of claim 10, wherein the method is performed prior to a surgical operation.

20. The method of claim 10, wherein the method is performed continuously during a surgical operation.

* * * * *